United States Patent [19]

MacGregor

[11] Patent Number: 4,579,120
[45] Date of Patent: Apr. 1, 1986

[54] STRAIN RELIEF FOR PERCUTANEOUS LEAD

[75] Inventor: David C. MacGregor, Miami, Fla.

[73] Assignee: Cordis Corporation, Miami, Fla.

[21] Appl. No.: 695,757

[22] Filed: Jan. 29, 1985

Related U.S. Application Data

[63] Continuation of Ser. No. 429,994, Sep. 30, 1982, abandoned.

[51] Int. Cl.$^4$ .............................................. A61M 25/02
[52] U.S. Cl. .................................... 128/640; 604/174; 604/180; 128/DIG. 26
[58] Field of Search ......................... 128/1 R, 783–786, 128/914, DIG. 26, 642, 639, 419 R, 419 P; 604/174, 180

[56] References Cited

U.S. PATENT DOCUMENTS

| | | | |
|---|---|---|---|
| 2,898,917 | 8/1959 | Wallace | 604/180 |
| 2,943,628 | 7/1960 | Howell | 128/640 |
| 3,187,745 | 6/1965 | Baum et al. | 128/639 |
| 3,387,608 | 6/1968 | Figar | 128/640 |
| 3,464,404 | 9/1969 | Mason | 128/640 |
| 3,487,837 | 1/1970 | Petersen | 604/180 |
| 3,518,984 | 7/1970 | Mason | 128/640 |
| 3,663,965 | 5/1972 | Lee, Jr. et al. | 128/1 R |
| 3,683,911 | 8/1972 | McCormick | 604/180 |
| 3,774,592 | 11/1973 | Lahr | 128/640 |
| 3,882,853 | 5/1975 | Gofman et al. | 128/DIG. 4 |
| 3,901,218 | 8/1975 | Buchalter | 128/DIG. 4 |
| 4,031,882 | 6/1977 | DeLuca | 128/642 |
| 4,080,970 | 3/1978 | Miller | 604/174 |
| 4,392,857 | 7/1983 | Beran | 128/DIG. 26 |

*Primary Examiner*—Edward M. Coven
*Attorney, Agent, or Firm*—Lockwood, Alex, Fitzgibbon & Cummings

[57] ABSTRACT

A member and method for anchoring and relieving the strain on a flexible, percutaneous lead which exits the body of a patient includes a flexible, elastomeric disc having a surface for contacting and conforming to the body of the patient. The surface is adhesively attached to the body at the location at which the lead exits the body. The opposite surface of the disc includes a bulbous shaped head. A passage extends through the adhesive, the disc and the head for snugly receiving the lead to extend therethrough. A slit may be provided in the disc between its perimeter and the passage for opening the disc to receive the lead in the passage and/or to remove the lead from the passage.

7 Claims, 4 Drawing Figures

U.S. Patent     Apr. 1, 1986     4,579,120
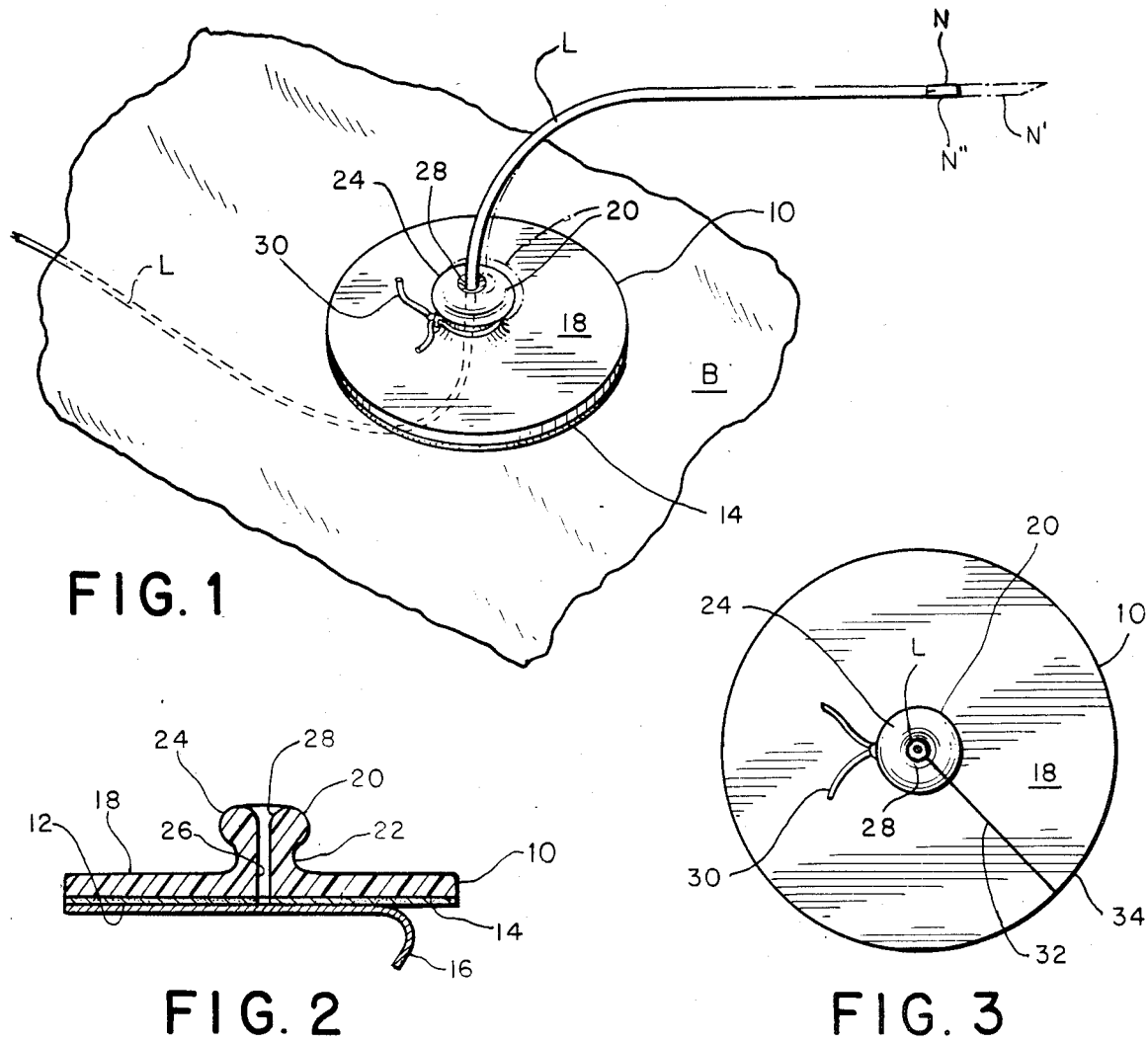
FIG. 1
FIG. 2
FIG. 3
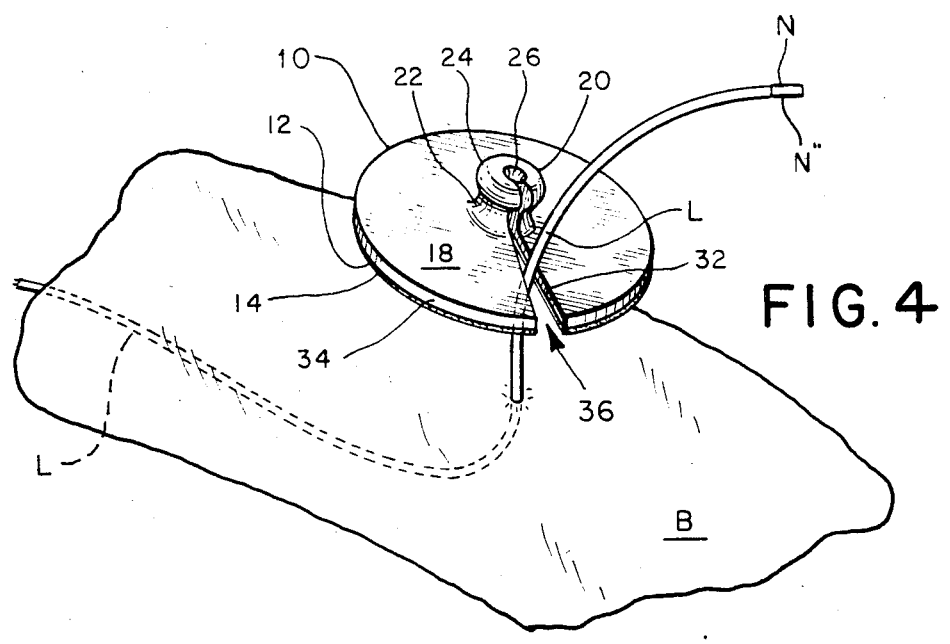
FIG. 4

STRAIN RELIEF FOR PERCUTANEOUS LEAD

This application is a continuation, of application Ser. No. 429,994, filed Sept. 30, 1982, now abandoned.

BACKGROUND AND SUMMARY OF THE INVENTION

The present invention relates to a member and method for anchoring and relieving the strain on a percutaneous lead and, more particularly, to a member and method for anchoring and relieving the strain on a flexible, conductive percutaneous lead where the lead exits the body of a patient.

Various flexible, percutaneous leads, have been employed in the past which extend into the body of a patient and exit the patient's body at some selected location on the body. Such leads, for example, may include electrically conductive temporary or permanent heart pacer leads or neural stimulator leads for stimulating the nervous system of the patient. One end of such lead, the end in the patient's body, is located at the location which is to be stimulated, for example the myocardium or in the epidural space surrounding the spinal cord. The conductive lead exits the body at a conveniently selected location and the other end of the lead is connected to a stimulator which may be carried on the exterior of the patient's body. The stimulator produces electrical signals which are transmitted through the lead to stimulate the tissue which is to be stimulated deep within the patient's body.

In the past, such percutaneous leads have been fixed in place at the location at which the lead exits the body by sutures in the skin at that location. Such suturing method of fixation has several disadvantages. One disadvantage is that strains which may be imparted to the lead during patient activity are transmitted to the sutured exit location and may cause movement or displacement of the lead and tearing of the skin by the sutures with attendant trauma to the patient. Another disadvantage is that the sutured exit is subject to infection, not only due to exposure of the sutures and lead(s) themselves, but also as a result of displacement of the lead due to strains which may be imparted to the lead and the sutures at the lead exit location during patient activity. Another disadvantage is the need for the sutures themselves, which are subject to infection, which may produce trauma, and which may result in puncturing of the insulation on the lead during placement of or strain on the sutures.

A member and method for anchoring and relieving the strain on such leads incorporating the principles of the present invention substantially reduces the likelihood of the occurrence of these disadvantageous consequences. A member and method incorporating the principles of the present invention firmly anchors and stabilizes the lead against movement at its exit location from the body during activity of the patient, thus substantially reducing the possibility of displacement of the lead or of infection or trauma resulting from such displacement and movement. The member and method incorporating the principles of the present invention also covers the lead exit to protect the exit against contamination which could lead to infection. The member and method incorporating the principles of the present invention is both simple to use, install and remove, and is inexpensive. The member and method incorporating the principles of the present invention firmly anchors the lead and may, in many cases, reduce, if not eliminate the need altogether for sutures for closure of the exit and the attendant disadvantages of such sutures.

In one principal aspect of the present invention, a member for anchoring and relieving the strain on a flexible, percutaneous lead which exits the body of a patient comprises a flexible disc having a first surface for contacting and conforming to the body of the patient at the location at which the lead exits the body, and a second surface opposite the first surface. An adhesive is located on the first surface for adhering the disc and its first surface to the body at the location at which the lead exits the body and over substantially the entire area of the first surface. A passage of substantially constant cross-section over its length extends through the thickness of the disc and opens through the first and second surfaces, the substantially constant cross-section being sized to snugly receive a lead which is also of substantially constant cross-section and such that the constant cross-section of the lead may be slidably positioned in the passage to extend beyond the first and second surfaces.

In another principal aspect of the present invention, the aforesaid member includes a bulbous shaped head projecting from the second surface of the disc and the passage extends into and opens through this head.

In still another principal aspect of the present invention, the aforementioned members may also include a slit through the disc extending from the perimeter of the disc to the passage, whereby the disc may be opened to be positioned around the head.

In still another principal aspect of the present invention, a method of anchoring and relieving the strain on a flexible, percutaneous lead which exits the body of a patient comprises positioning one end of the lead through the skin of the patient, positioning the portion of the lead which exits the patient's body to extend snugly through a passage through the thickness of a flexible disc such that the lead extends from both sides of the disc, shaping a surface of the disc to conform to the patient's body and positioning the surface against the body at the location where the lead exits the patient's body, and adhesively bonding the surface to the patient's body at the last mentioned location to anchor the disc and lead thereto.

In still another principal aspect of the present invention, the aforementioned method includes the disc having a bulbous shaped head projecting from a surface of the disc opposite the last mentioned surface, with the passage also extending into and opening through the head. The lead is positioned to extend through the passage in the head and is secured in the passage by binding a flexible thread means around the stem portion of the bulbous shaped head.

In still another principal aspect of the present invention, the aforementioned methods also include the disc having a slit extending from the perimeter of the disc to the passage, and the lead is positioned in the passage by opening the disc at the slit and sliding the lead through the open slit to the passage.

These and other objects, features and advantages of the present invention will be clearly understood through a consideration of the following detailed description.

BRIEF DESCRIPTION OF THE DRAWING

In the course of this description, reference will frequently be made to the attached drawing in which:

FIG. 1 is an overall perspective view of a member incorporating the principles of the present invention and for practicing the method of the present invention and in which the member is anchored to the body of a patient at the location at which the lead exits the body of the patient;

FIG. 2 is a cross-sectioned elevational view of the member shown in FIG. 1;

FIG. 3 is a plan view showing an alternative embodiment of member incorporating the principles of the present invention; and FIG. 4 is an overall perspective view of the altnerative embodiment shown in FIG. 3 in the process of being installed about the lead.

DESCRIPTION OF THE PREFERRED EMBODIMENTS

In FIGS. 1 and 2 one preferred embodiment of member for anchoring and relieving the strain on a flexbile, percutaneous lead at the location at which the lead exits the body of a patient is shown. The lead L may be one or more insulated conductors which are connected to a suitable stimulator (not shown). Where the lead is a heart pacer lead, the distal end of the lead which is to be positioned in the patient's heart may be terminated by a curved needle fastened to the conductor. The exterior, proximal end of the lead may be fastened to a straight needle N and, once the lead is ready for connection to the stimulator, the tip N' of the needle may be broken or cut off to leave a pin N" remaining which acts as a terminal as shown in FIG. 1. The stimulator generates selected electrical pulses or signals for stimulating certain locations inside the patient's body B and these pulses or signals are conducted through the lead L to those locations. By way of example, the end of the percutaneous lead in the patient's body B and its curved needle may be located in the patient's myocardium, in the case of a heart pacer, or the end of the lead may be located in the epidural space surrounding the patient's spinal cord, in the case of a neural stimulator.

The member preferably comprises a flexible disc 10 having a bottom surface 12, as shown in FIG. 2, which is capable of being flexed to contact and conform to the shape of the patient's body B at the location at which the lead L is to exit the body. The disc 10 could also be preshaped to conform to body contours. This surface 12 is coated over substantially its entire surface area with an adhesive layer 14 for adhering the surface 12 to the patient's body B at the lead exit location, as shown in FIGS. 1 and 2. Although it may not always be necessary, a backing 16, as shown in FIG. 2, is preferably included covering the adhesive 14 and protecting it against contamination prior to use and maintains the adhesive and surface 12 in a sterile condition. The backing 16 may be formed of a coated paper or a polymeric sheet material and is preferably peelable in a manner known to those skilled in the art so that it may be peeled from the adhesive layer 14 when the member is being readied for use. An antibiotic or other sterilizing substance may also be incorporated into the adhesive to help prevent sepsis.

The surface 18 of the disc 10, on the side of the disc opposite the surface 12, preferably includes a bulbous shaped head 20 substantially centered on the disc. The head 20 includes a narrower stem portion 22 and an upper wider portion 24. A substantially vertical passage 26 extends through the thickness of the disc 10 and, at its bottom end, opens through the surface 12 and its adhesive layer 14. The top of passage 26 opens through the top of the wider portion 24 of the head 20, as shown in FIG. 2, and is preferably flared at 28 at its point of exit from the head 20, as is also shown in FIG. 2. With the exception of the flare 28, the passage 26 is of substantially constant cross-section over its length. The cross-sectional shape of the passage is substantially identical to the cross-sectional shape of the lead L and the diameter of the passage 26 is sized so that it snugly fits the lead L when the lead is inserted through the passage as shown in FIG. 1.

Installation is accomplished by inserting the end of the lead L into the patient's body and positioning its end at the location to be stimulated, e.g. the heart, spinal cord, etc. By way of example, where the lead is a heart pacer lead, the end of the lead in the body typically terminates in a curved needle (not shown) which is inserted into the patient's myocardium. Once the lead has been positioned, the other end of the lead outside of the body is inserted upwardly through the passage 26 via needle N and the disc 10 is slid downwardly along the lead until it contacts the skin of the patient and conforms to the curvature of the patient's skin surface at the exit location. At this point, the disc 10 and its surface 12 are adhered to the body at the lead exit location with the adhesive layer 14 to anchor the disc 10 and the lead L firmly to the body. The lead L, which is also of substantially constant cross-section over its length, fits snugly in the passage 26.

The lead is preferably further secured by tying or binding with a suitable thread-like member, such as a suture 30, about the stem portion 22 of the bulbous shaped head 20, as shown in FIG. 1. Tying with the suture 30 not only seals the passage 26 against the entry of contaminants to protect against infection, but also firmly secures the lead L in the passage 26 against sliding or other displacement. Although a suture 30 is shown about the stem portion 22, it will be understood that other forms of fixation may be employed, such as a clamp, clip, applied adhesive, elastic band, etc. At this time, the tip N' of the needle N may be broken or cut off and the remaining portion N" of the needle may be coupled to a suitable stimulator (not shown).

A second alternative preferred embodiment of member is shown in FIGS. 3 and 4. The member in this embodiment is substantially identical to the member previously described and, thereby, the same reference numerals will be utilized to identify components which are substantially identical to each other in both of the embodiments.

The principal difference between the embodiments shown in FIGS. 3 and 4 and that shown in FIGS. 1 and 2 is that the embodiment in FIGS. 3 and 4 includes a slit 32 which extends through the thickness of the disc 10 and between the perimeter 34 of the disc and the passage 26 into and through the head 20. The slit 32 enables the disc 10 to be pulled apart to create a radially extending opening 36, as shown in FIG. 4, to allow the member to be assembled around or removed from the lead L after the lead has been fully inserted and positioned at its desired location in the body B of the patient and without the need to slide the exterior end of the lead through passage 26. This embodiment is particularly advantageous where the diameter of the terminal N" may be larger than the diameter of the lead L. Once the disc 10 has been positioned about the lead L at its exit from the body B of the patient and the lead has been positioned in the passage 26, the disc 10 and its surface 12 may be slid down the lead L, to the extent necessary, is flexed to conform to the surface of the body of the patient, and the disc is adhesively adhered to the body at the location of the exit of the lead from the body. The thread or suture 30 is then tied about the stem portion 22 of the bulbous shaped head 20 to secure the opening 36 produced by the slit 32 in its closed position and to snugly secure the lead L in the passage 26 to prevent the entry of contaminants through the passage and anchor the lead against movement.

The preferred embodiments of the invention which have been described are preferably formed by integrally molding the disc 10 and its bulbous shaped head 20 of a substantially flexible material of, for example, an elastomeric polymer, such as Silastic. The anchoring and strain relieving members are preferably quite flexible to allow conformation with the shape of the body of the patient at the location of exit of the lead and may be, for example, on the order of 55 Durometer in hardness.

It will be understood that although the disc 10 is shown as being substantially circular in shape, the shape of the disc may vary as desired and as may be preferable for certain applications. For example, the disc 10 may be square, rectangular, oval, or figure eight, in shape.

Although the lead L has been described as being a single electrical conductor, it is not intended that the present invention be limited only to use with such electrical conductors. It will be apparent that the principles of the invention may be practiced to anchor and relieve the strain of any elongate, flexible component with or without conductors or with more than one conductor, and which component is intended to enter the patient's body through the skin. For example, the lead L may comprise a catheter for fluids. Thus, the term "lead" as employed herein is intended to include any flexible percutaneous component, such as insulated or non-insulated electrical conductors, intravascular cardiac catheters, infusion, drainage or irrigation tubes for body cavities, ducts or cysts and abscesses, and pneumatic tubes for powering cardiac assist devices, artificial hearts, etc.

It will also be seen that the principles of the invention may be practiced where more than a single lead as shown is employed. Where multiple leads are employed, the bulbous shaped head 20 may include more than one passage 26 or may include plural heads 20 each with a single passage.

From the foregoing, it will be seen that the member and method described herein result in several advantages not present in the prior suturing methods of lead attachment. One such advantage is the reduction in the possibility of infection and trauma due not only to the seal which is effected by the member of the present invention at the location of exit of the lead from the patient's body after the member is installed, but also due to the anchoring and strain relief of the lead after installation and during activity of the patient. Strain forces which may be imparted to the lead L during activity of the patient tend to be dissipated not only by flexing of the bulbous shaped head 20, as shown by the dot and dash lines in FIG. 1, but these forces are also distributed over the area of the disc 10. The anchoring action of the present invention substantially minimizes, if not eliminates, the need for suturing of the lead at the exit location, thus reducing the possibility of patient infection and trauma or damage to the lead insulation. The present invention is capable of being quickly, easily and inexpensively fixed on the body of the patient and substantially reduces the possibility that the lead L might be moved or displaced after placement in the patient.

It will be understood that the embodiments of the present invention which have been described are merely illustrative of a few of the applications of the principles of the present invention. Numerous modifications may be made by those skilled in the art without departing from the true spirit and scope of the invention.

What is claimed is:

1. A system for anchoring and relieving strain on a flexible percutaneous lead which exits the body of a patient, comprising:

a one-piece molded retaining member including a stem portion of reduced diameter, a flexible disc portion of greater diameter at one end of said stem portion, and a bulbous head portion at the other end of said stem portion, said stem and bulbous portions being generally coaxial and perpendicular to said disc portion, said disc portion being generally flexible and having a generally flat exterior surface for contacting and conforming to the exterior of the patient's body adjacent the exit point of the percutaneous lead;

said flexible retaining member having an internal passage of substantially constant cross section extending longitudinally within said stem, disc and head portions of said retaining member, said passages being dimensioned to snuggly receive the percutaneous lead;

an adhesive layer on said exterior surface of said disc portion for adhering said retaining member to the body;

said bulbous head portion having a diameter greater than that of said stem portion such that said head and disc portions together define an annular recess region encircling the exterior of said stem portion; and compression means within said annular recess region and surrounding said stem portion for compressing said stem portion radially inwardly such that said passage is constricted around the lead whereby movement of the lead within the passage is restrained when said stem portion is compressed.

2. A lead anchoring system as defined in claim 1 wherein said compression means comprise a thread-like member disposed around and in contact with said stem portion within said annular recess region.

3. A lead anchoring system as defined in claim 2 wherein said adhesive layer includes an antibiotic therein.

4. A lead anchoring system as defined in claim 3 wherein said disc portion includes a radiallyextending slit extending from a point on the perimeter of said disc portion to said passage to enable said disc portion to be positioned around or removed from the percutaneous lead.

5. A lead anchoring system as defined in claim 4 wherein said thread-like member comprises a segment of suture constrictingly tied around said stem portion within said annular region.

6. A lead anchoring system as defined in claim 5 wherein said retaining member is formed of an elastomeric polymer.

7. A lead anchoring system as defined in claim 6 wherein said disc portion is substantially circular.

* * * * *